United States Patent [19]

Castagna

[11] Patent Number: 5,316,136
[45] Date of Patent: May 31, 1994

[54] CONDOM CASE WITH DUAL LOCKING MECHANISMS

[76] Inventor: Mary C. Castagna, 2002 Alta Vista, Austin, Tex. 78704

[21] Appl. No.: 22,256

[22] Filed: Feb. 24, 1993

[51] Int. Cl.$^5$ ............................................. B65D 85/14
[52] U.S. Cl. ...................................... 206/69; 206/1.5; 70/167; 70/339; 70/355; 220/210
[58] Field of Search ................. 206/69, 438, 1.5, 37, 206/38; 70/158, 163, 166, 167, 168, 169, 164, 165, 339, 337, 353, 355, 69; 220/210

[56] References Cited

U.S. PATENT DOCUMENTS

| | | | |
|---|---|---|---|
| 1,328,106 | 1/1920 | Stone | 70/69 |
| 2,233,699 | 3/1941 | Gorrell | 292/227 |
| 2,936,189 | 5/1960 | Pearson | 292/42 |
| 3,988,909 | 11/1976 | Catapano | 70/63 |
| 4,674,303 | 6/1987 | Salcone, II | 70/169 X |

Primary Examiner—Paul T. Sewell
Assistant Examiner—Jacob K. Ackun, Jr.
Attorney, Agent, or Firm—B. Noel Kivlin

[57] ABSTRACT

A condom case is provided that houses one or more condoms within an enclosure having two distinct and interdependent locking mechanisms. Two separate keys must be employed simultaneously to disengage the locking mechanisms and open the condom case. The condom case pragmatically protects the condom while symbolically promoting the concepts of mutual consent, fidelity, dignity, commitment and intimacy. The keys may be worn around the necks of each individual as an overt talisman of their exclusive relationship.

5 Claims, 6 Drawing Sheets

CONDOM CASE WITH DUAL LOCKING MECHANISMS

FIELD OF THE INVENTION

This invention relates to prophylactic device holders and cases.

SUMMARY OF THE INVENTION

A condom case is provided that houses one or more condoms within an enclosure having two distinct and interdependent locking mechanisms. In one embodiment, two separate keys must be employed simultaneously to disengage the locking mechanisms and open the condom case. The condom case pragmatically protects the condom while symbolically promoting the concepts of mutual consent, fidelity, dignity, commitment and intimacy. The keys may be worn around the necks of each individual as an overt talisman of their exclusive relationship.

These and other advantages are achieved with the present invention, in accordance with which a case for holding prophylactic devices comprises a base portion including an area for supporting a prophylactic device, a lid portion attachable to the base such that the prophylactic device is substantially surrounded by the base and lid portions, and first and second locking mechanisms for locking the lid portion to the base portion.

DETAILED DESCRIPTION

Figure 1:
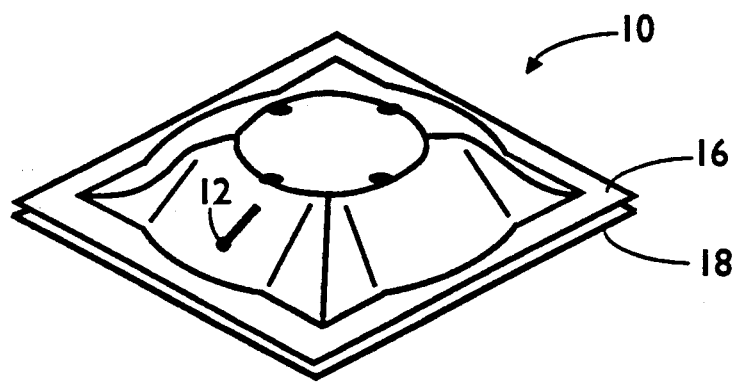
FIG. 1 is a perspective view of a condom case having two locking mechanisms.
Figure 2:
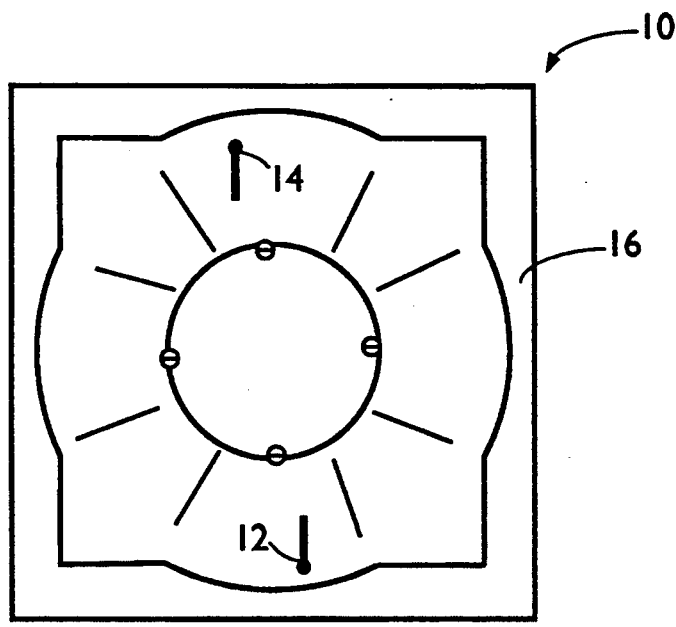
FIG. 2 is a top view of the condom case.
Figure 3:
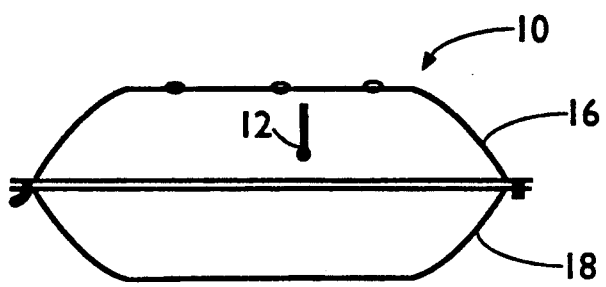
FIG. 3 is a side view of the condom case.

FIGS. 1-3 are perspective, top and side views of a condom case 10 including two interdependent locking mechanisms. The condom case includes a pair of key holes 12 and 14 to accommodate separate keys that disengage a pair of locking mechanisms within the case. An upper lid assembly 16 is detachable from a lower base or lid assembly 18 to expose an inner cavity that accommodates one or more packaged condoms. As will be better understood from the following, the locking mechanisms are provided within the upper lid assembly 16.

The condom case 10 is fabricated out of a variety of metals such as copper, sterling silver and stainless steel. In the embodiment of FIGS. 1-3, the upper and lower lids are fabricated out of copper. It is noted that alternative materials such as plastic or wood may be employed without departing from the spirit and scope of the invention.

Figure 4:
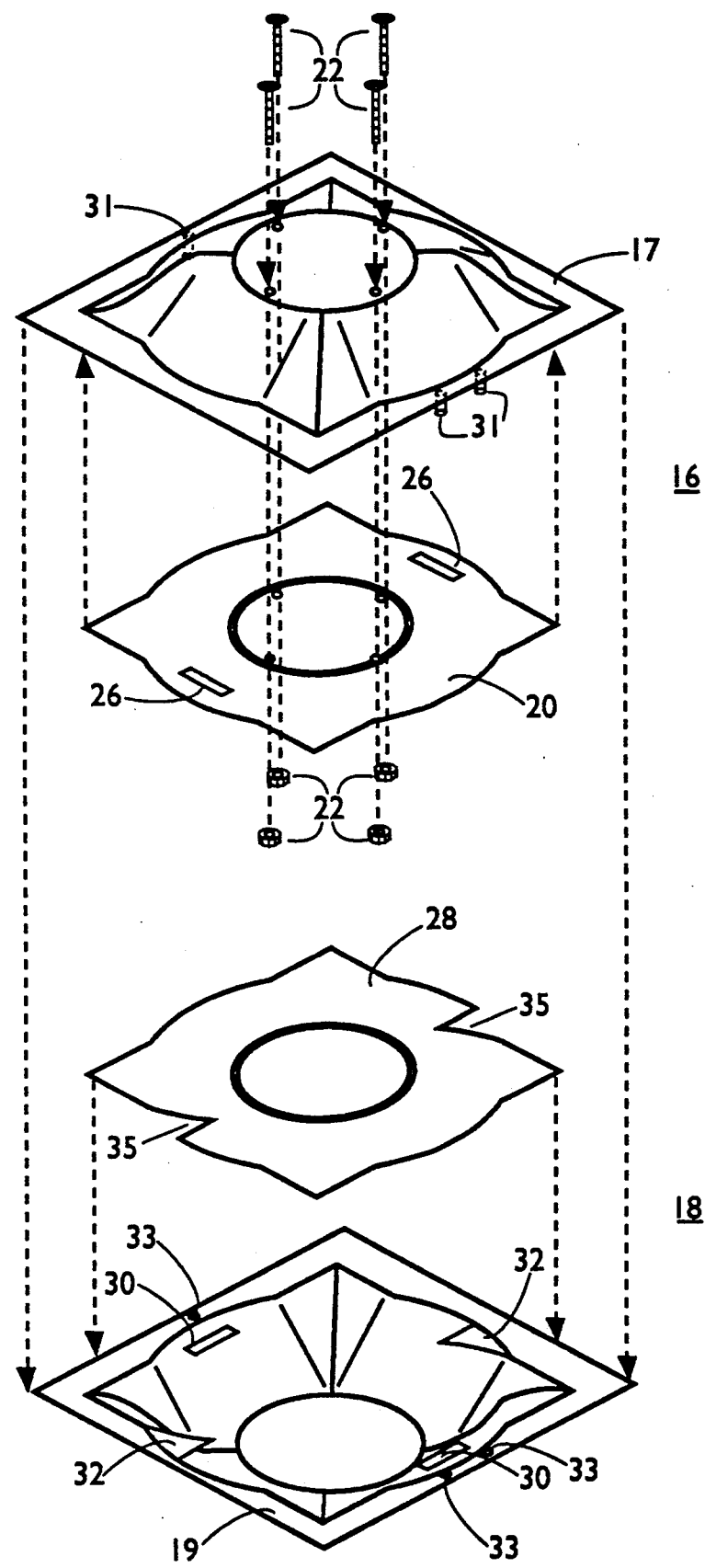
FIG. 4 is an exploded perspective view of the condom case.

FIG. 4 is an exploded perspective view that illustrates the interconnection of various components of the condom case 10. The upper lid assembly 16 includes an upper lid 17 that is secured to a protective plate 20 with a set of nuts and bolts 22. The locking mechanisms (not shown in this Figure) are mounted to underside portions of the upper lid 17 and are substantially enclosed between the upper lid 17 and the protective plate 20. A pair of open slots 26 are provided on the protective plate 20 and allow a catch arm of each locking mechanism to extend therethrough to accommodate the locking operation that secures the upper lid assembly 16 to the lower lid assembly 18.

The lower lid assembly 18 includes a support plate 28 that is secured with glue or solder to a pair of ledges 30 formed on a lower lid 19. The lower lid 19 is also formed with a pair of stationary catches 32 that extend from the upper side walls of the lower lid 19. It is noted that the support member 28 is provided with a pair of cut-out portions 35 that allow the support plate to be positioned beneath the stationary catches 32 upon the ledges 30.

The upper lid 17 includes a set of alignment or guide pins 31 that mate with a set of guide holes 33 provided on the lower lid 19. When the upper lid assembly 16 is appropriately positioned by a person on the lower lid assembly 18, the guide pins 31 penetrate the guide holes 33 and the catch arms of the locking mechanisms operatively engage with the stationary catches 32, as will be more evident from the following description. The support plate 28 is provided to allow a packaged condom to be placed thereon, and the protective plate 20 is provided to prevent damage to the packaged condom as a result of contact with the locking mechanisms within the upper lid assembly 16.

Figure 5:
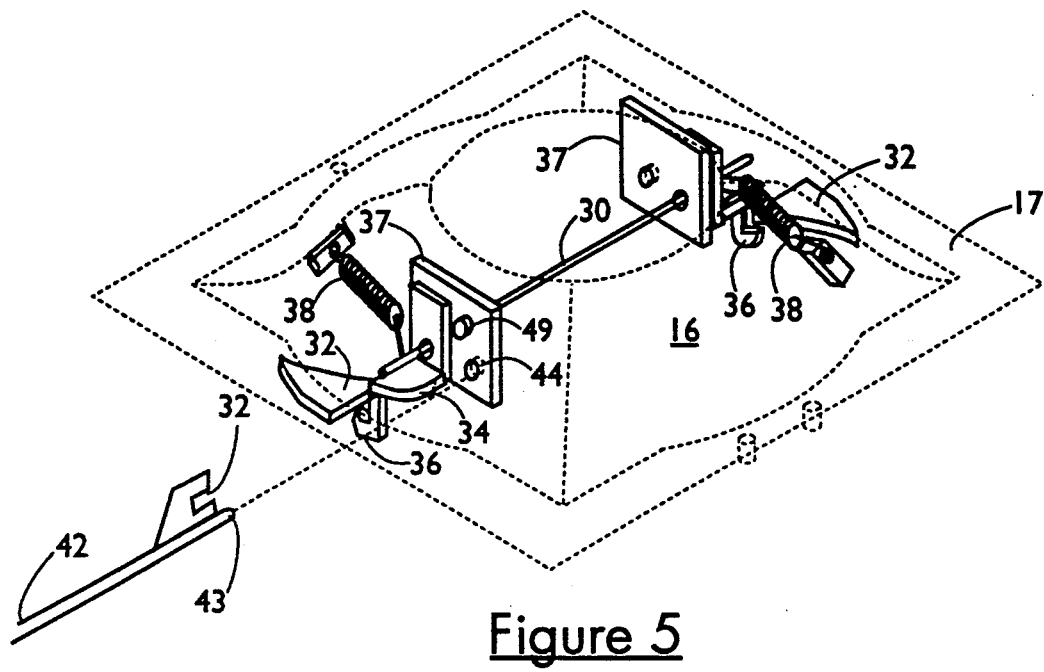
FIG. 5 is a perspective view of the locking mechanisms within the condom case.

FIG. 5 is a perspective view illustrating the locking mechanisms within the upper lid assembly 16. A rod member 30 is centered within an interior portion of the upper lid 17 and traverses opposite walls of the upper lid 17. The rod member 30 is supported by a pair of support fixtures 37 that are fixedly attached to the upper lid 17. A pivotal lock member 34 is operatively coupled to the rod member 30 and includes a catch arm 36 that engages or catches the respective stationary catch 32 of the lower lid assembly 18 when the case is in its locked position. A spring 38 is connected between the pivotal locking member 34 and the upper lid 17 to provide tension to the pivotal locking member 34.

Figure 6:
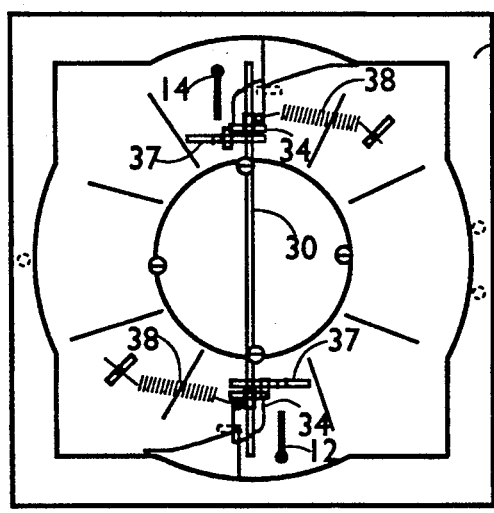
FIG. 6 is a top view of the locking mechanisms within the condom case.
Figure 7:
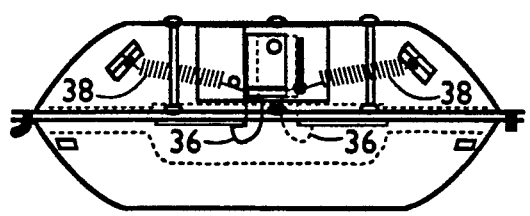
FIG. 7 is a side view of the locking mechanisms within the condom case.

FIGS. 6 and 7 are top and side views illustrating the locking mechanisms. When a person aligns the guide pins of the upper lid assembly 16 are aligned with the guide holes of the lower lid assembly 18, a lower curved portion of the catch arms 36 contact the edges of the respective stationary catch 32. As slight downward pressure is exerted by the person on the upper lid assembly 16, the pivotal locking members 34 swing slightly in a counterclockwise direction, allowing the catch arm 36 of each pivotal locking member 34 to catch beneath the respective stationary catch 35 to thereby engage in a locked position. It is noted that the tension provided by spring 38 causes the pivotal locking member 34 to snap back to its original position once the stationary catch 32 has cleared the hooked portion of the catch arm 36. This locking engagement occurs simultaneously for both locking mechanisms since the stationary catches 32 are positioned at similar locations on opposite sides of the lower lid 19.

Referring back to FIG. 5, when a key 42 is inserted horizontally into the key hole 12, a tip portion 43 of the key enters an interior guide hole 44 provided on the support fixture 37. When the appropriate key is rotated in a counterclockwise direction, a notched portion 48 of the key is not obstructed by a key block 49, and thus further rotation of the key is allowed. As rotation continues, the key contacts the side wall of the pivotal lock member 34, thereby causing a counterclockwise rotation of the pivotal lock member 34. This action also causes the catch arm 36 on the pivotal lock member 34 to swing in a conterclockwise direction, thereby releasing the catch arm 36 from the stationary catch 32. When both locking mechanisms are disengaged simultaneously, the bottom lid assembly may be separated from the top lid assembly. It is noted that in this embodiment, both locking mechanisms must be disengaged simultaneously with their appropriate keys to gain access to the condom that rests upon the support plate 28.

Figure 8:
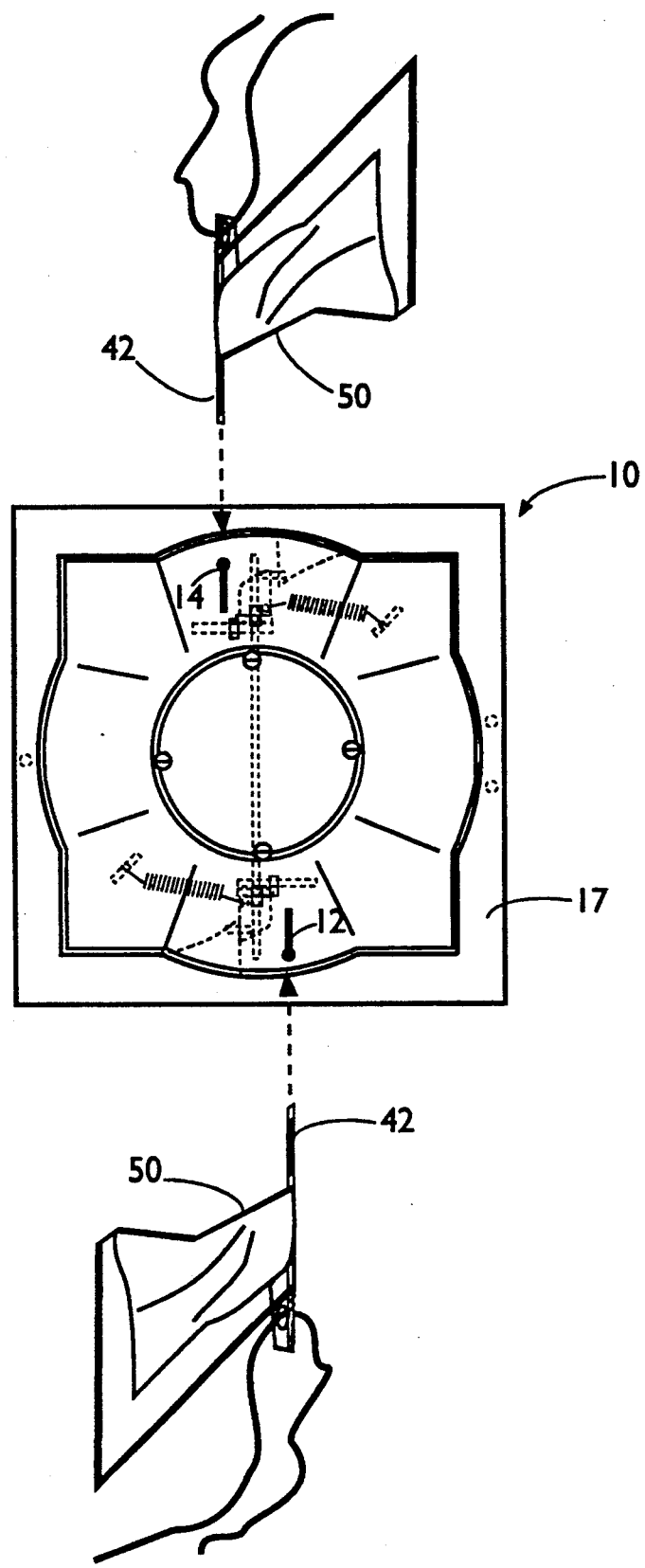
FIG. 8 is a top view of the condom case with a pair of keys to be inserted.
Figure 9:
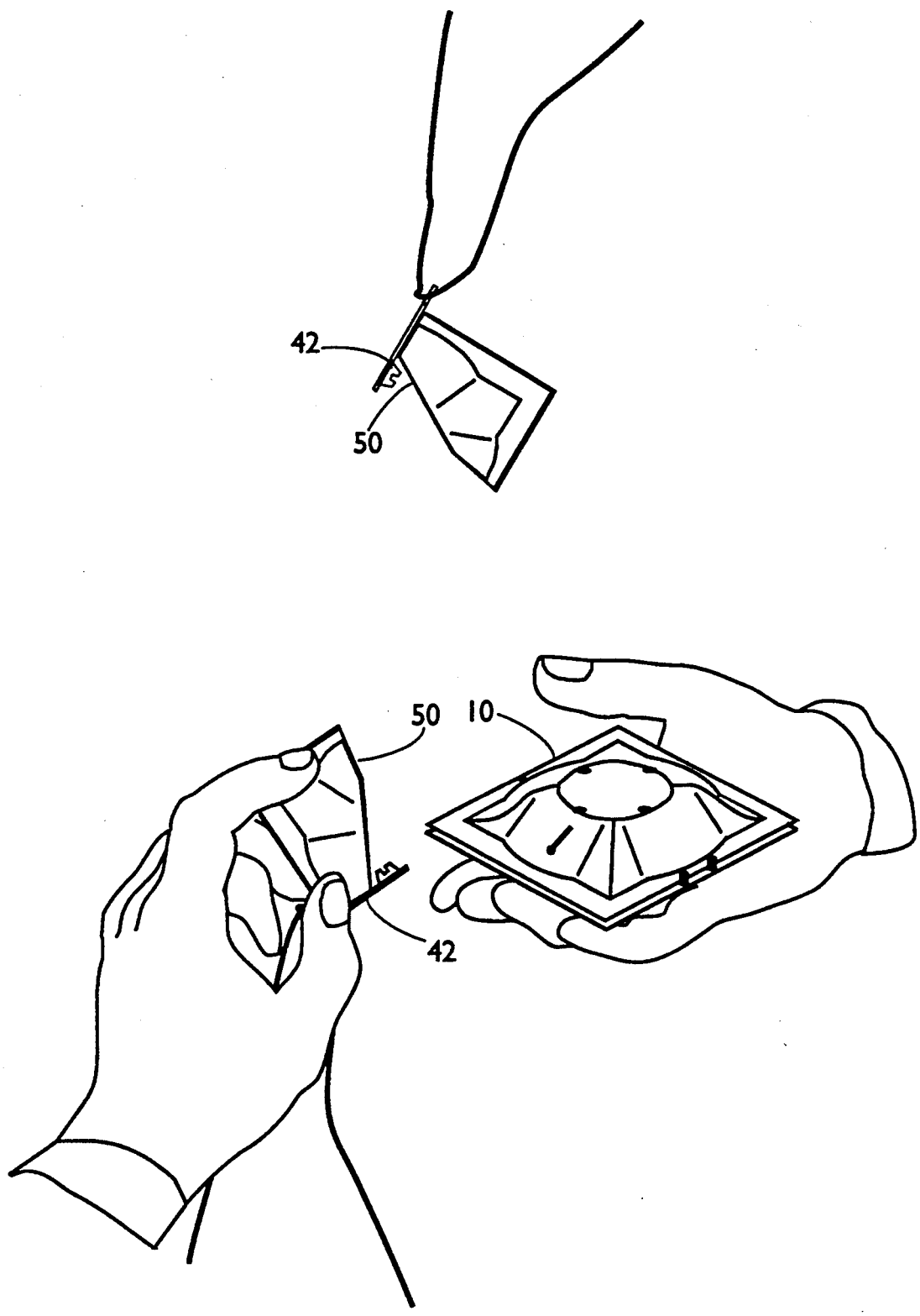
FIG. 9 is a perspective view of the condom case and keys.
Figure 10A:
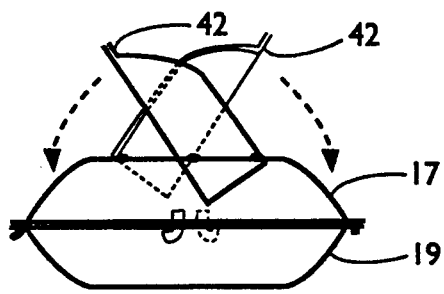
FIG. 10A and 10B are top and side views that illustrate the disengagement of the locking mechanisms.
Figure 10B:
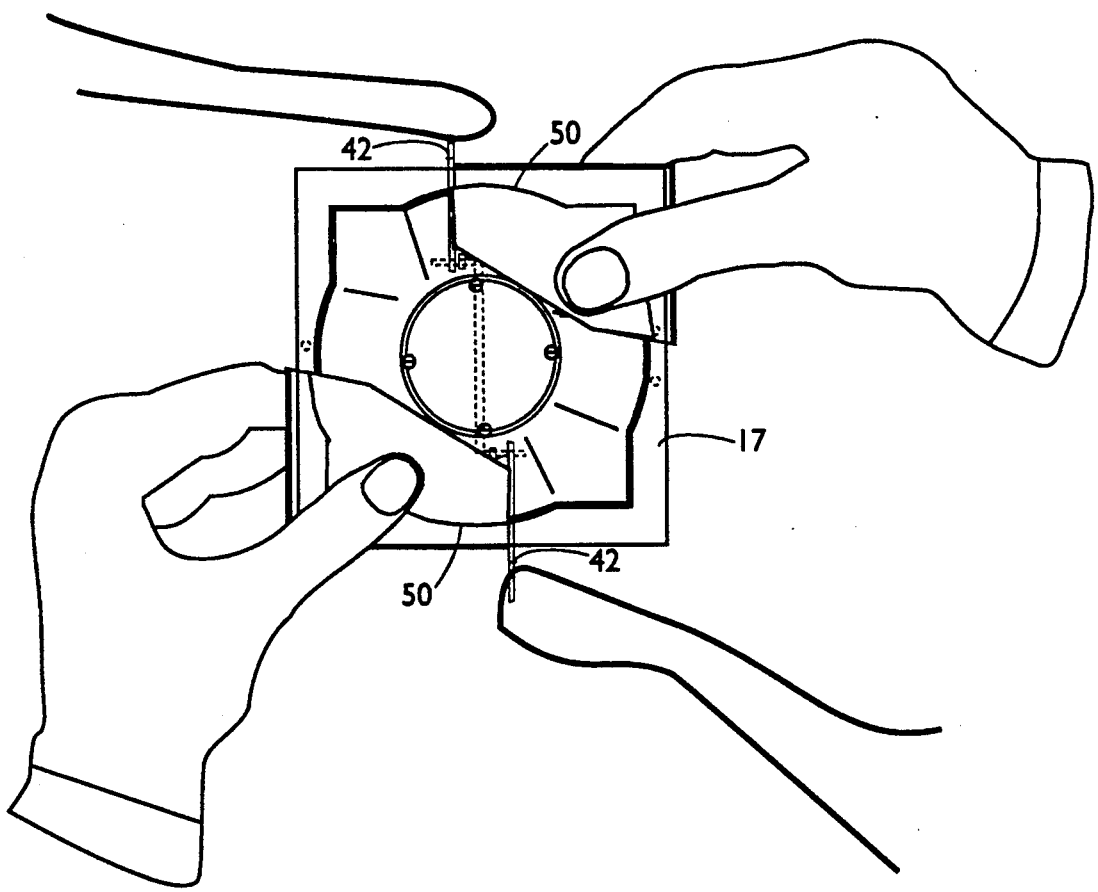

FIGS. 8 and 9 illustrate the condom case 10 with a pair of keys 42 to be inserted therein. In this embodiment, each key is formed with a flange portion 50 that is appropriately shaped to match an outer contour portion of the upper lid 17. After the keys have been inserted as illustrated in FIG. 10A, each key is rotated in a counterclockwise direction using the flange portion 50 as a handle. The locking mechanisms disengage when the surface contour of the flange portion 50 of each key abuts against the corresponding outer periphery of the upper lid 17, as illustrated in FIG. 10B. The upper lid assembly 16 may then be removed from the lower lid assembly 18 by exerting an upward force on the outer edges of the flange 50 of each key.

Numerous modifications and variations will become apparent to those skilled in the art once the above disclosure is fully appreciated. For example, the upper lid assembly 16 could be hinged to the lower lid assembly 18 rather than being completely detachable. In addition, variations of the locking mechanisms could be employed. It is to be understood that the above detailed description of the preferred embodiment is intended to be merely illustrative of the spirit and scope of the invention and should not be taken in a limiting sense. The scope of the claimed invention is better defined with reference to the following claims.

What is claimed is:

1. In combination, a condom case and keyset comprising:
   a first key;
   a second key; and
   a palm-sized case comprising:
      a base portion including an area for supporting a condom;
      a lid portion attachable to said base portion, wherein said lid portion includes a first key hole for accommodating said first key and a second key hole for accommodating said second key;
      a first locking mechanism for locking said lid portion to said base portion, wherein said first locking mechanism includes a first reciprocating catch member, a first spring, and a first stationary catch member wherein said first reciprocating catch member is positioned such that said first reciprocating catch member is capable of latching with said first stationary catch member when said lid portion is placed upon said base portion, and wherein said first reciprocating catch member is movable away from said first stationary catch member such that said first reciprocating catch member unlatches from said first stationary catch member when said first key is inserted and engaged within said first key hole; and
      a second locking mechanism for locking said lid portion to said base portion, wherein said second locking mechanism includes a second reciprocating catch member, a second spring, and a second stationary catch member wherein said second reciprocating catch member is positioned such that said second reciprocating catch member is capable of latching with said second stationary catch member when said lid portion is placed upon said base portion, and wherein said second reciprocating catch member is movable away from said second stationary catch member such that said second reciprocating catch member unlatches from said second stationary catch member when said second key is inserted and engaged within said second key hole;
   wherein said first spring is coupled to said first reciprocating catch member and wherein said second spring is coupled to said second reciprocating catch member such that both said first key and said second key must be engaged simultaneously within said first and second key holes, respectively, to unlock said lid portion from said base portion.

2. The condom case and keyset as recited in claim 1 wherein said first reciprocating catch member includes a hooked portion for contacting against and thereby latching with said first stationary catch member.

3. The condom case and keyset as recited in claim 2 wherein said first spring applies a force to said first reciprocating catch member such that the hooked portion of said catch member remains latched with said first stationary catch member when said first key is not engaged within said first key hole.

4. In combination, a condom case and keyset comprising:
   a first key including a non-planar flange portion forming a handle thereof;
   a second key including a non-planar flange portion forming a handle thereof; and
   a palm-sized case comprising:
      a base including an area for supporting a condom;
      a lid attachable to said base, wherein said lid includes a first key hole for accommodating said first key and a second key hole for accommodating said second key;
      a first locking mechanism for locking said lid to said base; and
      a second locking mechanism for locking said lid to said base;
   wherein the non-planar flange portion of said first key is shaped to substantially match a first outer contour portion of said lid and wherein the non-planar flange portion of said second key is shaped to substantially match a second outer contour portion of said lid; and wherein said lid is unlocked from said base when said flange portion of each key is rotated to abut its matching outer contour portion on said lid.

5. In combination, a condom case and keyset comprising:
   a first key including a non-planar flange portion forming a handle thereof;

a second key including a non-planar flange portion forming a handle thereof; and a palm-sized case comprising:
- a base including an area for supporting a condom;
- a lid attachable to said base, wherein said lid includes a first key hole for accommodating said first key and a second key hole for accommodating said second key;
- a first locking mechanism for locking said lid to said base, wherein said first locking mechanism includes a first reciprocating catch arm, a first spring, and a firs stationary catch member wherein said first reciprocating catch arm is positioned such that said first reciprocating catch arm is capable of latching with said first stationary catch member when said lid is placed upon said base, and wherein said first reciprocating catch arm is movable away from said first stationary catch member such that said first reciprocating catch arm unlatches from said first stationary catch member when said first key is inserted and rotated within said first key hole;
- a second locking mechanism for locking said lid to said base, wherein said second locking mechanism includes a second reciprocating catch arm, a second spring, and a second stationary catch member wherein said second reciprocating catch arm is positioned such that said second reciprocating catch arm is capable of latching with said second stationary catch member when said lid is placed upon said base, and wherein said second reciprocating catch arm is movable away from said second stationary catch member such that said second reciprocating catch arm unlatches from said second stationary catch member when said second key is inserted and rotated within said second key hole;

wherein said first spring is coupled to said first reciprocating catch arm and wherein said second spring is coupled to said second reciprocating catch arm such that both said first key and said second key must be engaged simultaneously within said first and second key holes, respectively, to unlock said lid from said base; and wherein the non-planar flange portion of said first key is shaped to substantially match a first outer contour portion of said lid and wherein the non-planar flange portion of said second key is shaped to substantially match a second outer contour portion of said lid.

* * * * *